(12) United States Patent
Franke et al.

(10) Patent No.: US 8,884,070 B2
(45) Date of Patent: Nov. 11, 2014

(54) ENERGY EFFICIENT SYNTHESIS OF ALIPHATIC ALDEHYDES FROM ALKENES AND CARBON DIOXIDE

(75) Inventors: Robert Franke, Marl (DE); Dirk Fridag, Haltern am See (DE); Bart Hamers, Dorsten (DE); Horst-Werner Zanthoff, Muelheim a.d. Ruhr (DE); Matthias Blug, Witten (DE); Julia Strautmann, Mannheim (DE); Stefan Nordhoff, Recklinghausen (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 13/703,925

(22) PCT Filed: Jun. 16, 2011

(86) PCT No.: PCT/EP2011/060021
§ 371 (c)(1),
(2), (4) Date: Feb. 27, 2013

(87) PCT Pub. No.: WO2011/157788
PCT Pub. Date: Dec. 22, 2011

(65) Prior Publication Data
US 2013/0178657 A1 Jul. 11, 2013

(30) Foreign Application Priority Data
Jun. 17, 2010 (DE) .......................... 10 2010 030 209

(51) Int. Cl.
*C07C 45/50* (2006.01)
*C07C 45/00* (2006.01)

(52) U.S. Cl.
CPC .............. *C07C 45/00* (2013.01); *C07C 45/50* (2013.01)
USPC ........................................ 568/449; 568/450

(58) Field of Classification Search
USPC ................................................ 568/449, 450
See application file for complete search history.

(56) References Cited

U.S. PATENT DOCUMENTS

| 6,914,162 B2* | 7/2005 | Richter et al. ............. 568/451 |
| 2004/0024259 A1 | 2/2004 | Richter et al. |
| 2008/0033223 A1 | 2/2008 | Sigl et al. |
| 2011/0130595 A1 | 6/2011 | Lueken et al. |
| 2012/0123169 A1 | 5/2012 | Kaizik et al. |
| 2012/0190895 A1 | 7/2012 | Kaizik et al. |

FOREIGN PATENT DOCUMENTS

| DE | 10 2004 041 850 | 3/2006 |
| DE | 10 2005 061 642 | 7/2006 |
| EP | 2 206 694 B1 | 2/2014 |
| WO | 02 02496 | 1/2002 |
| WO | WO2004/041763 A1 | 5/2004 |
| WO | 2009 146985 | 12/2009 |
| WO | 2010 105892 | 9/2010 |
| WO | 2011 038957 | 4/2011 |
| WO | 2012 041846 | 4/2012 |
| WO | 2012 062558 | 5/2012 |
| WO | 2012 065833 | 5/2012 |

OTHER PUBLICATIONS

U.S. Appl. No. 13/822,650, filed Mar. 13, 2013, Franke, et al.
U.S. Appl. No. 13/988,431, filed May 20, 2013, Nordhoff, et al.
U.S. Appl. No. 13/883,808, filed May 7, 2013, Franke, et al.
Tominaga, K.I., "An environmentally friendly hydroformylation using carbon dioxide as a reactant catalyzed by immobilized Ru—complex in ionic liquids," Catalysis Today, vol. 115, pp. 70-72, (2006).
Fujita, S.I., et al., "Hydroformylation of Cyclohexene with Carbon Dioxide and Hydrogen Using Ruthenium Carbonyl Catalyst: Influence of Pressures of Gaseous Components," International Journal of Molecular Sciences, vol. 8, pp. 749-759, (2007).
Sakakura, T., et al., "Transformation of Carbon Dioxide," Chemical Reviews, vol. 107, pp. 2365-2387, (2007).
Esswein, A.J., et al., "Hydrogen Production by Molecular Photocatalysis," Chemical Reviews, vol. 107, pp. 4022-4047, (2007).
International Search Report Issued Sep. 16, 2011 in PCT/EP11/60021 Filed Jun. 16, 2011.
Kotohiro Nomura and Yasukazu Saito: n-Alkene and Dihydrogen Formation from n Alkanes by Photocatalysis using Carbonyl (chloro) phosphine Rhodium Complexes. J. Chem. Soc. Chem. Commun, 1988, 161ff.

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

Provided is a process for producing an aldehyde from an alkylene. The process includes (a) photocatalytically dehydrogenating at least one alkane to obtain a mixture comprising at least one olefin and hydrogen, (b) adding carbon dioxide and hydrogen to the mixture, and (c) hydroformylating the olefin to at least one aldehyde. The process also includes converting carbon dioxide and hydrogen into water and carbon monoxide prior to the hydroformylating. In addition, the conversion of carbon dioxide and hydrogen into water and carbon monoxide is performed by a reverse water gas shift reaction.

18 Claims, No Drawings

ENERGY EFFICIENT SYNTHESIS OF ALIPHATIC ALDEHYDES FROM ALKENES AND CARBON DIOXIDE

Aldehydes such as valeraldehyde (pentanal) for example are widely used industrial chemicals. Pentanal is currently produced on a large industrial scale by hydroformylation of the olefins 1-butene or 2-butene by addition of synthesis gas (carbon monoxide and hydrogen). The butenes come from petrochemical processes, the synthesis gas is likewise produced from fossil sources.

Given the restricted industrial utility of fossil sources of raw materials and the view that the $CO_2$ concentration in the atmosphere is climate damaging, there has long been a need for alternative ways to produce aldehydes such as pentanal by minimising the use of resources and cutting $CO_2$. Besides, the carbon monoxide needed for the hydroformylation process presents increasing acceptance issues in the general public because of its undoubted toxicity.

The problem addressed by the present invention is therefore that of specifying a process for producing aldehydes which, compared with conventional hydroformylation, cuts $CO_2$, which utilises alternative sources of raw materials, and which has no need for a step of providing carbon monoxide.

This problem is solved by processes comprising the following steps:
a) providing at least one alkane;
b) photocatalytically dehydrogenating the alkane to a mixture comprising at least one olefin and hydrogen;
c) adding carbon dioxide and hydrogen to the mixture;
d) hydroformylating the olefin to at least one aldehyde.

A first underlying idea of the present invention is to use the hydrogen released in the photocatalytic dehydrogenation of alkanes for the subsequent hydroformylation of the olefin formed by the dehydrogenation. The hydrogen requirements of the hydroformylation can therefore be partly covered energy-efficiently from the $CO_2$-neutral photocatalysis. In addition, the photocatalysis uses butanes as a starting material, which are available relatively cheaply compared with the butenes currently used. Petrochemically obtained butane currently is mostly routed into thermal recovery with $CO_2$ being emitted.

The invention secondly rests on the realisation that the hydrogen from the catalytic dehydrogenation makes it possible to use $CO_2$ as carbon source for the hydroformylation in place of CO. This is accomplished for example by means of a reverse water gas shift reaction using the $CO_2$, which is not wanted in the atmosphere, and the free hydrogen to produce the CO needed for the hydroformylation in situ. There is no need for a separate supply of the toxic CO and, what is more, $CO_2$ generated in other processes can be used as a raw material, reducing carbon dioxide emissions as a whole.

The invention accordingly makes it possible for $CO_2$ to be returned into the chemical value chain by substituting $CO_2$ for the hitherto needed carbon monoxide, which is obtained from synthesis gas. Each tonne of the product aldehyde needs more than half a tonne of $CO_2$ in the case of valeraldehyde. Given a global production of 340 000 t of valeraldehyde a year, this amounts to cutting the $CO_2$ output by about 200 000 t of $CO_2$ a year. In addition, there are other aldehydes produced by this process, making a multiple of this potential likely.

The two process segments which have been combined according to the present invention—"photocatalytic dehydrogenation" and "hydroformylation with carbon dioxide"—are each separately described in the literature as feasible:

K. Nomura and Y. Saito, in J. Chem. Soc., Chem. Commun, (1988), 161 describe the photocatalytic dehydrogenation of alkanes under mild conditions and radiation over a rhodium catalyst:

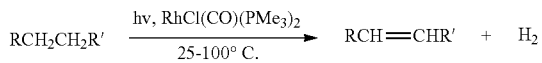

Further directions for conducting a photocatalysis are given by:
a) A. J. Esswein, D. G. Nocera, Hydrogen Production by Molecular Photocatalysis, Chem. Rev. 2007, 107, 4022-4047;
b) D. Morales-Morales, R-Redón, C. Yung C. M Jensen, Dehydrogenation of alkanes catalyzed by an iridium phosphinito PCP pincer complex, Inorg. Chim. Acta, 2004, 357, 2953-2956;
c) M. J. Burk, R. H. Crabtree, D. V. McGrath, J. Chem. Soc., Chem. Commun. 1985, 1829-1830;
d) M. J. Burk, R. H. Crabtree, J. Am. Chem. Soc. 1987, 109, 8025-8032;
e) T. Sakakura, T. Sodeyama, Y. Tokunaga, M. Tanaka, Chem. Lett. 1988, 263-264;
f) K. Nomura, Y. Saito, J. Chem. Soc., Chem. Commun. 1988, 161;
g) J. A. Maguire, W. T. Boese, A. S. Goldman, J. Am. Chem. Soc. 1989, 111, 7088-7093;

K. Tominaga and Y. Sasaki disclose a hydroformylation with carbon dioxide in Catal. Commun., 1, 2000, 1 as follows:

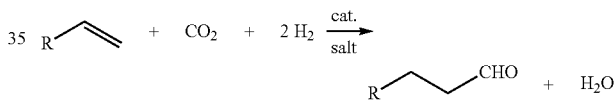

Multinuclear ruthenium complexes such as $Ru_3(CO)_{12}$ for example are preferably used as catalyst for the hydroformylation with $CO_2$.

In addition, salts such as LiCl, LiBr, LiI, NaCl, KCl or mixtures thereof can be added as promoters. This appears to be advantageous because hydrohalic acids (HCl, HBr, . . . ) formed from the salts in situ act as proton donors and thus mediate the reverse water gas shift reaction.

Further useful directions for conducting the hydroformylation with $CO_2$ are given in:
a) K. Tominaga, Y. Sasaki, K. Hagihara, T. Watanabe, M. Saito, Chem. Lett. 1994, 1391-1394;
b) K. Tominaga, Y. Sasaki, J. Mol. Catal. A: Chem. 2004, 220, 159-165;
c) K. Tominaga, Catal. Today 2006, 115, 70-72;
d) S. Fujita, S. Okamura, Y. Akiyama, M. Arai, Int. J. Mol. Sci. 2007, 8, 749-759.

The process according to the invention is preferably used to convert the alkane n-butane via photocatalytic dehydrogenation to the olefin 1-butene and $H_2$ and to subject this mixture to a hydroformylation with $CO_2$ to convert the 1-butene into the aldehyde pentanal.

The overall process based on n-butane and $CO_2$ comprises the basic steps of photocatalytic dehydrogenation and hydroformylation with $CO_2$:

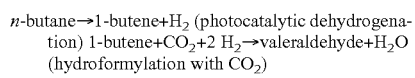

Valeraldehyde can subsequently be used in the currently already industrially established processes on a large scale to produce industrial chemicals such as polymer additives.

For $CO_2$ to be used as a raw material, the hydroformylation must be preceded by a conversion of carbon dioxide and hydrogen into water and carbon monoxide, preferably by way of a reverse water gas shift reaction.

In a preferred development of the invention, the conversion of carbon dioxide and hydrogen into water and carbon monoxide and the hydroformylating take place in a conjoint reactor and/or over a conjoint catalyst.

A preferred embodiment is characterized by the use of an immobilised catalyst in the photocatalytic dehydrogenating and/or in the hydroformylating and/or in the conversion of carbon dioxide and hydrogen into water and carbon monoxide. An immobilised catalyst is a homogeneous catalytic system which is coupled to an insoluble support material in order that the catalyst, which has a homogeneous action, may be separated from the reaction mixture like a heterogeneous catalyst. The immobilisation is accomplished using ionic liquids:

Ionic liquids—called ILs hereinafter—are low-melting salts (<100° C.) and are used as novel solvents for extraction processes and catalysis for example. One key reason why ILs have aroused industrial as well as academic interest is the fact that they have an extremely low vapour pressure, which virtually rules out solvent losses. With regard to using ionic liquids in the field of catalysis, two approaches have very recently been pursued in particular:

ILs are interesting solvents for heterogeneous catalysed reactions as well as homogeneous catalysis. For instance, Xu et al.

(D.-Q. Xu, Z.-Y. Hu, W.-W. Li, S.-P. Luo, Z.-Y. Xu Hydrogenation in ionic liquids: An alternative methodology toward highly selective catalysis of halonitrobenzenes to corresponding haloanilines, J. of Mol. Cat. A: Chem. 2005, 235, 137-142.)

have been able to show that ILs are interesting media for the hydrogenation of halogenated nitrobenzenes to the corresponding halogenated anilines over Raney nickel, carbon-supported platinum and palladium catalysts. When ILs are used as solvents, the undesired dehalogenation is reduced compared with organic solvents.

Similarly, the supported ionic liquid phase (SILP) concept is very promising. A thin film of an IL with a homogeneous catalyst dissolved therein is applied to the surface of a porous (inert) solid by physisorption for example. This evades disadvantages of homogeneous two-phase catalysis because the IL quantity needed is reduced and mass transfer effects are avoided by the thin film. To coat the porous support, the IL is dissolved in a solvent (dichloroethane for example) together with the homogeneous catalyst and then the solid support is added to the solution. The solution was then gradually freed of the volatile dichloromethane under reduced pressure. This method of preparation ensures that the IL fully penetrates into the pores. To produce systems having a higher or lower degree of pore fillage, or layer thicknesses, the IL concentration in the dichloromethane solution can be increased or reduced, respectively. The SILP concept has already been successfully tested for some reactions.

Further expositions concerning SILP and its use in catalysis are discernible for a person skilled in the art from:

a) A. Riisager, P. Wasserscheid, R. v. Hal, R. Fehrmann, Continous fixed-bed gas-phase hydroformylation using supported ionic liquid phase (SILP) Rh catalysts, J. Catal. 2003, 219, 452-455;

b) Riisager, K. M. Eriksen, P. Wasserscheid and R. Fehrmann, Propene and 1-Octene Hydroformylation with Silica-Supported, Ionic Liquid-Phase (SILP) Rh-Phosphine Catalysts in Continuous Fixed-Bed Mode, Catal. Letters 2003, 90, 149-153;

c) C. P. Mehnert, R. A. Cook, N. C. Dispenziere, M. Afeworki, Supported Ionic Liquid Catalysis—A New Concept for Homogeneous Hydroformylation Catalysis, J. Am. Chem. Soc. 1998, 120, 12289-12296;

d) C. P. Mehnert, E. J. Molzeleski, R. A. Cook, Supported ionic liquid catalysis investigated for hydrogenation reactions, Chem. Comm. 2002, 24, 3010-3011;

e) A. Wolfson, I. F. J. Vankelecom, P. A. Jacobs, Co-immobilization of transition-metal complexes and ionic liquids in a polymeric support for liquid-phase hydrogenations, Tetrahedron Lett. 2003, 44, 1195-1198;

f) C. M. Gordon, New developments in catalysis using ionic liquids, Appl. Catal. A: General 2001, 222, 101-117;

g) P. J. Dyson, Transition metal chemistry in ionic liquids, Trans. Met. Chem. 2002, 27, 353-358;

h) D. Zhao, M. Wu, Y. Kou, E. Min, Ionic liquids: applications in catalysis, Cat. Today 2002, 74, 157-189;

i) J. Dupont, R. F. de Souza, P. A. Z. Suarez, Ionic Liquid (Molten Salt) Phase Organometallic Catalysis, Chem. Rev. 2002, 102, 3667-3692;

j) H. Olivier-Bourbigou in Catalysis in Nonaqueous Ionic Liquids in Multiphase Homogeneous Catalysis (B. Cornils et al. Eds.), Wiley VCH, Weinheim, Germany, 2006, 407-603;

k) M. J. Earle, P. B. McCormac, K. R. Seddon, The first high yield green route to a pharmaceutical in a room temperature ionic liquid, Green Chem. 2000, 2, 261;

l) B. Hamers, P. S. Bäuerlein, C. Müller, D. Vogt, Hydroaminomethylation of n-Alkenes in a Biphasic Ionic Liquid System, *Adv. Synth. Catal.* 2008, 350, 332-342;

m) H. Wong, S. Han, A. G. Livingston, The effect of ionic liquids on product yield and catalyst stability, Chem. Eng. Sci. 2006, 61, 1338-1341.

n) K. Anderson, P. Goodrich, C. Hardacre. D. W. Rooney, Heterogeneously catalysed selective hydrogenation reactions in ionic liquids, Green Chem. 2003, 5, 448-453. k) D.-Q. Xu, Z.-Y. Hu, W.-W. Li, S.-P. Luo, Z.-Y. Xu Hydrogenation in ionic liquids: An alternative methodology toward highly selective catalysis of halonitrobenzenes to corresponding haloanilines, J. of Mol. Cat. A: Chem. 2005, 235, 137-142.

A further concept is the solid catalyst with ionic liquid layer (SCILL) concept for improving the selectivity of heterogeneous catalysts. The SCILL concept—cf.

a) U. Kernchen, B. Etzold, W. Korth, A. Jess, Solid Catalyst with Ionic Liquid Layer (SCILL)—A New Concept to Improve the Selectivity Investigated for the Example of Hydrogenation of Cyclooctadiene. Chem. Eng. Technol. 2007, 30, 985-994.

b) N. Wörz, J. Arras, P. Claus, Influence of ionic liquids on continuous hydrogenation of citral in trickle bed reactor [in German], Annual Reaction Technology Symposium at Würzburg, 10.-12.5.2010, transaction volume pages 34/35— combines and to some extent expands on the two strategies described above: of the SILP technology, a porous solid is coated with an ionic liquid, but now the solid is a heterogeneous catalyst and not just an inert support intended to immobilise the homogeneous catalyst dissolved in the IL. Thus, there is no homogeneous catalyst involved in the SCILL concept, although a combination with the SILP concept is an option for integrating homogeneous and heterogeneous catalysis. The IL layer is stable and there is no leaching of the IL into the organic phase.

In addition to the possibility of a homogeneous catalyst being immobilised by the IL on a porous support, the ionic liquid can also have a direct influence on the kinetics of the reaction. This holds particularly when the solubility of the reactants and/or intermediates is different. For instance, in the sequential heterogeneously catalysed hydrogenation of cyclooctadiene (COD) into cyclooctene (COE) and cyclooctane (COA), the coating with an ionic liquid (butylmethylimidazolium octylsulphate) leads to a distinct increase in the selectivity for the COE intermediate. This is attributable to the poor solubility of the intermediate, among other factors. A similar effect is likely for the reverse water gas shift reaction ($H_2+CO_2 \rightarrow CO+H_2O$) which is important to the present invention, since $CO_2$ is likely to have the best solubility in ILs among the four reactants involved, which will have a positive influence on this reaction, which is equilibrium limited at relatively low temperatures.

The fundamental problem of homogeneous catalysis—how to remove the catalyst from the reaction material—is thus solved according to the present invention by the above-described SILP and/or SCILL concept by immobilising the developed homogeneous catalysts using ionic liquids.

This concept can also be applied to the photocatalytic conversion of alkanes. Porous glasses can be used as support material in order that very deep penetration of the light may be ensured. The catalyst used for the photocatalytic dehydrogenation of the alkanes is thus preferably supported by a porous glass.

EXAMPLE

The invention will now be more particularly elucidated using the preparation of valeraldehyde (pentanal) from n-butane as an example:

In accordance with the present invention, n-butane is initially dehydrogenated photocatalytically and the resulting 1-butene reacted with $CO_2$ in a hydroformylation to form the valeraldehyde.

This overall process looks as follows:

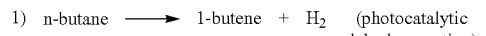
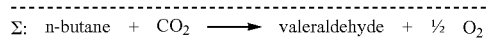

Steps 2a and 2b can take place in one reactor and/or ideally over one catalyst, and therefore can be regarded as a $CO_2$ hydroformylation as follows:

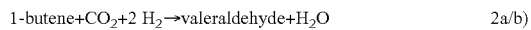

Even without a photocatalytic dehydrogenation of butane, i.e. on the basis of butene, the process would still be advantageous over the "usual" CO-based hydroformylation if the hydrogen can be provided in a $CO_2$-neutral fashion:

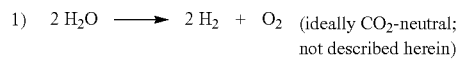
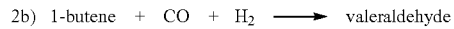
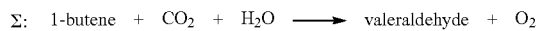

Catalysts suitable for photocatalysis are organic and organometallic photosensitisers based on iridium and rhodium, or combination catalysts consisting of a photosensitiser component and a proton reduction component based on Pd, Ru, Ir or Fe.

Catalysts suitable for hydroformylation are iridium-phosphine complexes, ruthenium-based complexes, more particularly multinuclear ruthenium complexes and also iron hydride carbonyl complexes. Salts such as LiCl, LiBr, LiI, NaCl, KCl can additionally be added alone or in mixtures as promoters.

The homogeneous catalytic systems can be immobilised on solid porous supports of differing pore size using ionic liquids. Porous glasses can be used as supports to increase the transmissivity to light.

The invention claimed is:
1. A process for producing an aldehyde from an alkylene, the process comprising:
   a) photocatalytically dehydrogenating at least one alkane to obtain a mixture comprising at least one olefin and hydrogen;
   b) adding carbon dioxide and hydrogen to the mixture; and
   c) hydroformylating the olefin to at least one aldehyde, and further comprising converting carbon dioxide and hydrogen into water and carbon monoxide prior to the hydroformylating,
   wherein the conversion of carbon dioxide and hydrogen into water and carbon monoxide is performed by a reverse water gas shift reaction.
2. The process of claim 1, wherein
   the alkane is n-butane,
   the olefin is 1-butene, and
   the aldehyde is valeraldehyde.
3. The process of claim 1, wherein the conversion of carbon dioxide and hydrogen into water and carbon monoxide and the hydroformylating are performed in a conjoint reactor, over a conjoint catalyst, or both in a conjoint reactor and over a conjoint catalyst.
4. The process of claim 1, wherein the photocatalytic dehydrogenating, the hydroformylating, or both, are performed by contacting a reactant with an immobilized catalyst.
5. The process of claim 4, wherein the catalyst is immobilized using an ionic liquid.
6. The process of claim 5, wherein the catalyst used for the photocatalytically dehydrogenating is supported by a porous glass.
7. The process of claim 4, wherein the catalyst for the hydroformylating is a multinuclear ruthenium complex.
8. The of claim 1, further comprising adding at least one salt during the hydroformylating.
9. The process of claim 1, wherein the photocatalytic dehydrogenating is performed by contacting a reactant with an immobilized catalyst.
10. The process of claim 1, wherein the hydroformylating is performed by contacting a reactant with an immobilized catalyst.

11. The process of claim 1, wherein both the photocatalytic dehydrogenating and the hydroformylating are performed by contacting a reactant with an immobilized catalyst.

12. The process of claim 1, wherein the conversion of carbon dioxide and hydrogen into water and carbon monoxide is performed by contacting the carbon dioxide and the hydrogen with an immobilized catalyst.

13. The process of claim 1, wherein the photocatalytic dehydrogenating, the hydroformylating, and the conversion of carbon dioxide and hydrogen into water and carbon monoxide are each performed by contacting a reactant with an immobilized catalyst.

14. The process of claim 4, wherein the conversion of carbon dioxide and hydrogen into water and carbon monoxide and the hydroformylating are performed in a conjoint reactor, over a conjoint catalyst, or both in a conjoint reactor and over a conjoint catalyst.

15. The process of claim 7, wherein the multinuclear ruthenium complex is $Ru_3(CO)_{12}$.

16. The process of claim 8, wherein the salt is selected from the group consisting of LiCl, LiBr, LiI, NaCl, and KCl.

17. The process of claim 1, further comprising converting the carbon dioxide and hydrogen into water and carbon monoxide, wherein the converting and the hydroformylating are performed in a single reactor.

18. The process of claim 17, wherein the converting and the hydroformylating are performed over a single catalyst.

* * * * *